United States Patent [19]

Ralston, Jr.

[11] 4,349,024
[45] Sep. 14, 1982

[54] MULTIPLE ADAPTER DEVICE FOR INTERCONNECTING TUBING OF DIFFERENT SIZES

[76] Inventor: Philip G. Ralston, Jr., 364 N. 835 East, Lindon, Utah 84062

[21] Appl. No.: 249,818

[22] Filed: Apr. 1, 1981

[51] Int. Cl.³ .............................................. A61M 3/00
[52] U.S. Cl. .................................... 128/247; 128/348
[58] Field of Search ........ 128/247, 348, 351, 275-278; 285/DIG. 22, 260, 283

[56] References Cited

U.S. PATENT DOCUMENTS

| | | | |
|---|---|---|---|
| 3,058,472 | 10/1962 | Thornton, Jr. | 128/348 |
| 3,282,476 | 11/1966 | Tracy | 222/484 |
| 3,633,586 | 1/1972 | Sheridan | 128/351 |
| 3,667,781 | 6/1972 | Holbrook | 128/275 |
| 3,731,684 | 5/1973 | Spiegel | 128/247 X |

*Primary Examiner*—John D. Yasko
*Attorney, Agent, or Firm*—Philip A. Mallinckrodt

[57] ABSTRACT

A multiple adapter device is provided for use with a variety of tubular connectors. A body member adapted for connection to a catheter or container is provided with an adapter passage therethrough of a diameter convenient for use with relatively large connectors likely to be encountered during use of the catheter or container to which the device is attached. A flexible strap is secured on one end to the body member and extends outwardly. An adapter member having an adapter passage therethrough and having an outside diameter corresponding to the body member passage is secured to the strap a sufficient distance from the body member to permit the adapter member to be inserted into the body member passage by folding the strap. The adapter member passage has a diameter convenient for use with smaller connectors likely to be encountered during use of the catheter or container to which the device is attached. A plug sized to fit the adapter member passage is secured to the strap farther along its length at a sufficient distance from the adapter member to permit the plug to be inserted into the adapter member passage by folding the strap.

8 Claims, 6 Drawing Figures

MULTIPLE ADAPTER DEVICE FOR INTERCONNECTING TUBING OF DIFFERENT SIZES

BACKGROUND OF THE INVENTION

1. Field

The invention is in the field of adapter devices for interconnecting tubing of different sizes, but is particularly concerned with such adapter devices as used with medical appliances.

2. State of the Art

In the medical arts, it is common to employ a variety of syringes and tubes to transfer liquids from one container to another or into a catheter which is connected to a patient. It is also common to transfer a gas, such as oxygen, through a tube from a container in which it is stored to a breathing mask, tent structure, or the like.

One particular use for a catheter connected to a patient is as a feeding tube. For this purpose the catheter is typically passed through the nose and esophagus and into the stomach of a patient. Such a catheter is generally provided with an external, end fitting adapted to receive a luer-type connector attached to a tube having its other end connected to a feeding bag containing a liquid to be introduced into the patient's stomach.

In the use of feeding tubes, it is often desirable to be able to aspirate gastric juices from a patient's stomach. This is generally done by connecting a relatively large syringe to the feeding tube and partially withdrawing the plunger so as to form a vacuum. However, the tip of a large syringe will not fit into a connection fitting adapted to accept a luer-type connector.

Thus, in the past, the end fitting of a feeding tube has been adapted to receive a large syringe, and a short adapter tube has been provided for insertion into the end fitting. Such adapter tube accepts in turn the tip of a small syringe or the luer-type connector of a feeding bag. Although this arrangement is workable, it is necessary to remove the adapter tube before a large syringe can be connected to the end fitting of the feeding tube, and it is not uncommon for the adapter tube to be lost or misplaced.

It is also desirable to be able to seal the end fitting when the feeding tube is not in use, so that foreign objects do not enter the feeding tube, and so that stomach contents are prevented from escaping through the tube. In the past, a separate plug was provided, but more recently a plug connected to the feeding tube end fitting by a flexible strap has been effectively employed. However, when using a plug connected to a flexible strap, it is necessary to remove the adapter tube from the end fitting before the plug can be inserted, again providing opportunity to lose or misplace the adapter tube.

SUMMARY OF THE INVENTION

The present invention provides a multiple adapter device suited for use in place of a conventional catheter end fitting and which is capable of receiving more than one size or type of connector. It includes a plug to seal the device when desired, and effectively avoids the problems encountered when using a separate adapter tube that may be easily lost or misplaced.

The device has a body member provided with an adapter passage therethrough of a diameter convenient for use with the larger connectors which are likely to be encountered during use of the particular type of catheter or container to which the multiple adapter device is attached. One end of a flexible strap is attached to the body member and extends away from the body member. An adapter member having an outerside diameter approximately the same as, or slightly larger than the diameter of the body member passage is attached to the flexible strap at such a distance from the body member as makes it convenient to insert the adapter member into the body member passage by folding or bending the strap. The adapter member also has an adapter passage therethrough of a diameter convenient for use with smaller connectors likely to be encountered during use of the catheter or container to which the device is attached. The strap extends past the adapter member, and a plug that is sized to fit snugly into the adapter member passage is attached to the flexible strap at a distance farther along the strap, whereby it can be inserted into the adapter member passage by folding or bending the strap, thus sealing the device. When the adapter and plug are both inserted into the body member and the adapter member passages, respectively, the strap approximates a flattened S in shape.

THE DRAWINGS

In the accompanying drawings, which represent the best mode presently contemplated for carrying out the invention:

FIG. 1 is a perspective view of an adapter device of the invention attached to a catheter and showing, in phantom, a relatively large tube interconnected thereby with the catheter;

FIG. 2, a similar view of the same adapter device shown as interconnecting a smaller size tube with the catheter;

FIG. 3, a similar view of the same device showing how the plug is used;

FIG. 4, a vertical section taken along the line 4—4 of FIG. 1;

FIG. 5, a vertical section taken along the line 5—5 of FIG. 2; and

FIG. 6, a vertical section taken along the line 6—6 of FIG. 3.

DETAILED DESCRIPTION OF THE ILLUSTRATED EMBODIMENT

Figures 1, 2, 3:
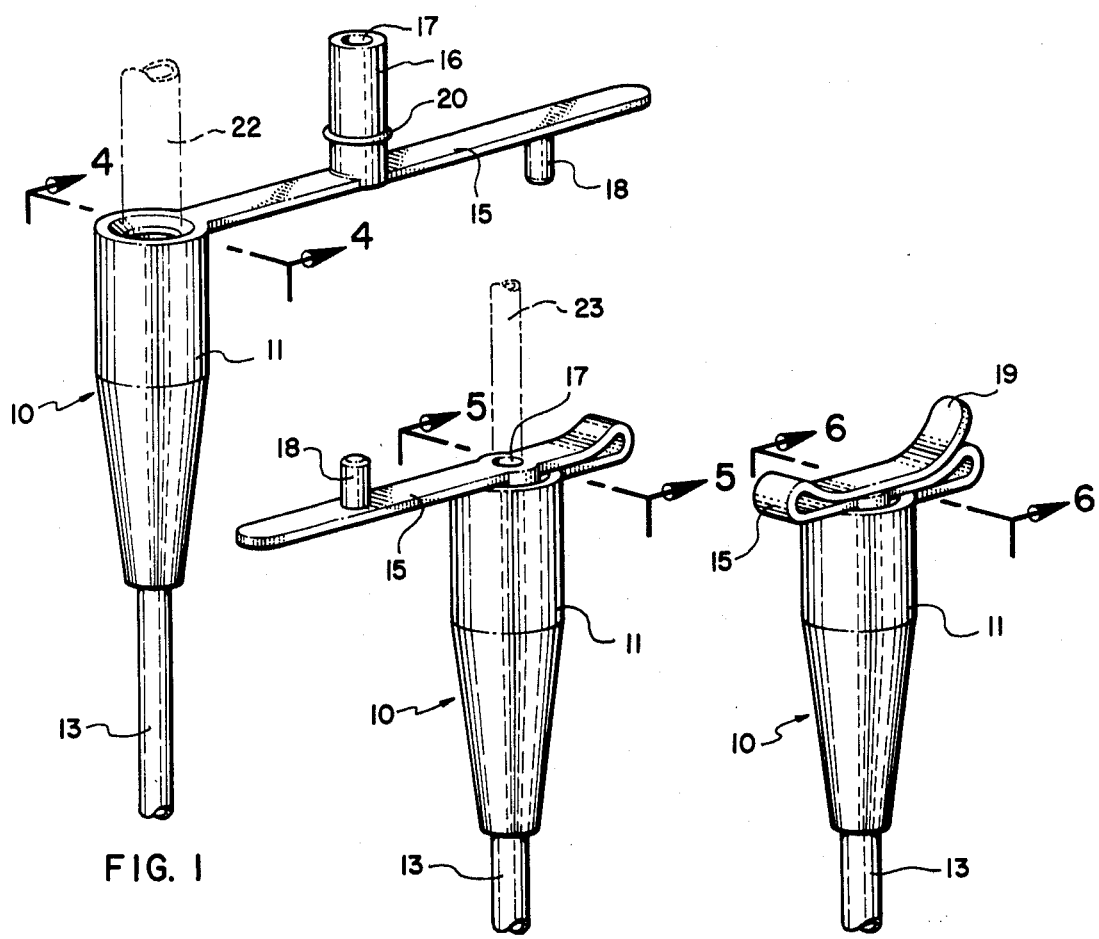
Figures 4, 5, 6:
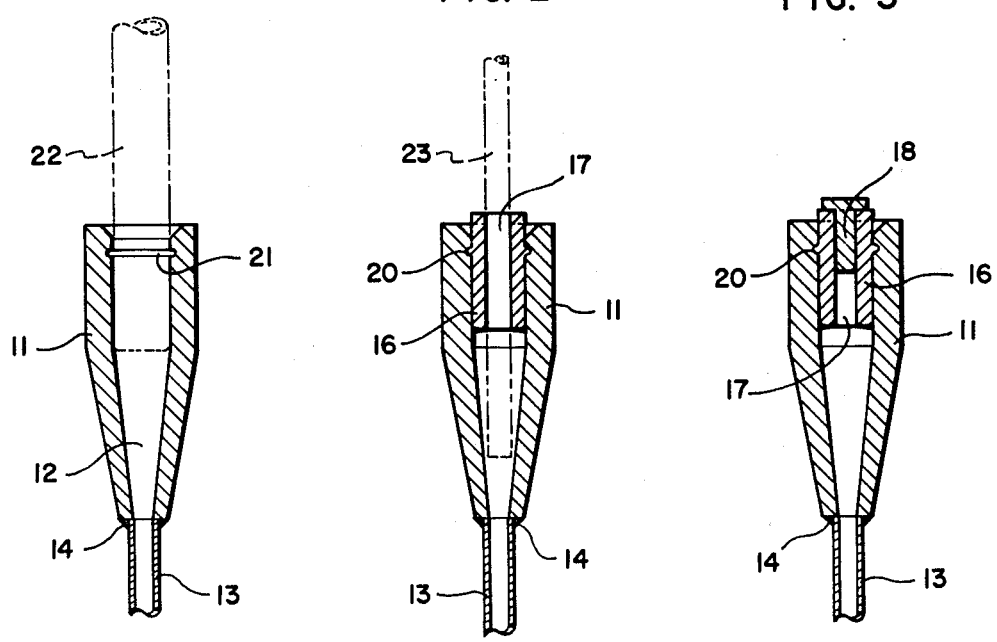

The presently preferred embodiment of the multiple adapter device, shown generally at 10 includes a tapered tubular body member 11, having an adapter passage 12 therethrough and being attached at its smaller end to a catheter 13, as by use of an adhesive 14, although it should be understood that the body member could also be attached to a container or the like; a flexible strap 15 which is secured at one end to the body member 11; a tubular adapter member 16, which also has an adapter passage 17 therethrough, attached to strap 15 at a sufficient distance from body member 11 whereby folding or bending of the strap allows the adapter member to be inserted into the passage 12 of the body member; and a plug member 18 attached to strap 15 at a sufficient distance farther along the length of the strap whereby folding or bending of the strap allows the plug to be inserted into passage 17 of the adapter member.

In order to facilitate insertion of adapter member 16 into passage 12, such adapter member of this preferred embodiment is attached to the top of the strap 15 so that it extends away from the strap in a direction opposite that in which it will point when inserted into passage 12. This arrangement necessitates passage 17 of the adapter member passing through the strap as well as through adapter member 16. Plug member 18 is attached to the side of the strap opposite the side to which the adapter member is secured. Thus, folding the strap at one particular point along its length places the adapter member in position for insertion into passage 12, and folding the strap at another point places plug member 18 in position for insertion into passage 17. When the adapter member and the plug member are both inserted, into passages 12 and 17, respectively, the strap approximates a flattened S in shape, see FIG. 3.

In order to facilitate removal of plug 18, it is desirable to extend strap 15 somewhat past the plug so as to provide a tab 19 which can be easily grasped.

The multiple adapter device is conveniently used with a variety of connectors. The passage 12 through the body member of this preferred embodiment is cylindrical in shape through about one-half the length of the body member and is a convenient diameter for use with relatively large connectors likely to be encountered during use of the particular product to which the device is attached. When the device is secured to a catheter 13 having a smaller diameter than the open end of the body member passage, as is the case in the illustrated embodiment, it is preferred that passage 12 of body member 11 be tapered inwardly to the size of the catheter 13, as shown.

The multiple adapter device is preferably molded in one piece of a soft, flexible material, such as silicone or a thermoplastic. This allows the device to expand somewhat when a connector is inserted into one of the passages, and thereby results in a more secure, liquid-tight seal. It is also important that strap 15 be flexible so that it may be folded in the manner described above and shown in FIGS. 2 and 3. It should be understood, however, that strap 15 could be a wire, filament, or other structure that serves to connect or link the adapter member and plug member to the body member.

The outside diameter of adapter member 16 should be about the same size as the diameter of passage 12, or perhaps slightly larger. To aid in sealingly securing the adapter member in the body member passage, the adapter member may be provided with a raised annular bead 20 which is received by a corresponding groove 21 in the body member passage when the adapter member is fully inserted.

The passage 17 through the adapter member may be cylindrical as shown, or may optionally be tapered. It should be of a convenient size for use with relatively small connectors which are likely to be encountered when using the particular product to which the multiple adapter device is attached.

When a connector of an appropriate type is inserted into the adapter member passage 17, the adapter member will preferably be expanded slightly, thus improving the seal and securing it more positively in the base member passage 12.

The plug member 18 has a diameter approximately the same or slightly larger than the diameter of passage 17, whereby the plug member will be held securely in place when inserted into the adapter member passage.

For use with large connectors, the adapter member is removed from the body member passage 12 and a large connector is inserted. Such a large connector, shwon in phantom as 22, may be a catheter, a tube, the tip of a syringe, or other tubular object which can be inserted into the base member passage. It is also possible to use a connector having a taper, so long as it can be held securely in a substantially leak-proof manner. To aid in sealingly securing a large connector, such a connector may be forced somewhat into the area where the body member passage tapers inwardly.

Use of small connectors is similar to use of large connectors. Again, the small connector can be a catheter, tube, the tip of a syringe, or other tubular object which can be inserted into the adapter member passage 17 when the adapter member is itself inserted into the body member passage 12. A small connector is shown in phantom as 23. As with a large connector, a small connector should fit securely and sealingly in the multiple adapter device. Again, the small connector may be tapered and may be inserted until it is wedged somewhat into the taper of the body member passage 12.

The purpose of the invention is to provide a multiple adapter device which may be attached to a catheter or container, and which may be easily used with a variety of connectors.

For example, the device 10 may be secured to a catheter 13 designed for use as a feeding tube. Typically, a feeding tube catheter, known as a nasogastric feeding tube, is inserted through a nostril of a patient that is either unconscious or too weak to eat, and placed into the patient's stomach. When using such a nasogastric feeding tube, it is desirable to have the versatility of being able to connect the feeding tube to various devices. For instance, it is desirable at times to be able to remove stomach contents so as to determine the amount of acidity in the stomach, so as to determine whether materials fed through the tube are being absorbed, or for other reasons. This is most conveniently done by inserting a large volume syringe, having a relatively large tip, into the body member passage 12, and withdrawing the syringe plunger, thus forming a partial vacuum and thereby aspirating stomach contents.

At other times, it is preferred to use a connector having a smaller diameter. For instance, when administering medications orally, it is preferable to use a small-volume, small-tip syringe which can conveniently be inserted into the adapter member passage. At other times, a standard "luer" connector may be used with the adapter member passage. Typically, a feeding bag containing liquid nourishment is provided with a standard luer connector.

Nasogastric feeding tubes are preferably made from silicone, because silicone is biologically inert and causes little or no irritation to the sensitive mucosal and esophageal membranes with which it comes in contact. By constructing the multiple adapter device of the same material, or a similar material, it will have the same or similar stretch and flexibility characteristics, thereby forming a more secure and reliable junction between the multiple adapter device 10 and the catheter 13.

More than one adapter member might be provided by a variety of arrangements. For example, more than one flexible strap may be attached to the body member, each having an adapter member with a passage of diameter different from the other adapter member passages, and each having a plug adapted to fit into its respective adapter member passage. Another alternative would be to have several adapter members secured to a single strap, each having an outside diameter corresponding to the body member passage, but each having a different size of passage therethrough and having a single plug which is sized to fit one of the adapter member passages.

Yet another alternative would be to have the outside diameter of each adapter member sized so that it could be inserted into the passage of the next larger adapter member. The plug member could then be sized to fit the passage of the smallest adapter member. The largest adapter member would be sized to fit the passage of the body member.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. An adapter device for use with at least two different sizes of connectors, comprising a body member having a passage therethrough for accepting a particular size of connector therein; flexible linking means, one end of which is secured to said body member; an adapter member capable of being received by the body member passage, said adapter member having a passage therethrough for accepting a connector of a size different than that accepted by the body passage, said adapter member being secured to the linking means intermediate its length in a manner such that bending of said linking means permits insertion of the adapter member into the body member passage; and plug means capable of being received by the adapter member passage, said plug means being secured to the linking means near that end thereof which is not secured to the body member in a manner such that bending of the linking means permits insertion of the plug means into the adapter member passage.

2. A device according to claim 1, wherein the linking means is a strap.

3. A device according to claim 2, wherein the adapter member is secured to one side of the strap and extends from said strap in a direction opposite the direction it points when inserted into the passage of the body member, the passage of said adapter member also passing through said strap; and wherein the plug means is secured to the side of the strap opposite the side to which the adapter member is secured.

4. A device according to claim 3, wherein the strap extends past the plug means to serve as a tab for grasping when removing the plug means from the passage of the adapter member.

5. A device according to claim 1 or 3, wherein the passage of the body member is provided with an annular groove, and the adapter member is provided with a corresponding annular bead, whereby the adapter member is held securely in place in sealing engagement when inserted into the passage of the body member.

6. A device according to claim 1 or 3, wherein the device is molded in one piece of silicone.

7. A device according to claim 1 or 3, wherein the device is molded in one piece of a thermoplastic.

8. A device according to claim 1 or 3, wherein the body member is attached to a catheter.

* * * * *